United States Patent
Kipp et al.

(10) Patent No.: US 6,221,222 B1
(45) Date of Patent: Apr. 24, 2001

(54) REFERENCE ELECTRODE SOLUTION CONTAINING ORGANIC AMMONIUM AND PHOSPHONIUM SALTS FOR POTENTIOMETRIC MEASUREMENT OF PH

(75) Inventors: James Kipp, Wauconda; Glenn Wehrmann, Waukegan; Richard Hammond, Grayslake; Christine Rebbeck, Algonquin, all of IL (US)

(73) Assignee: Baxter International Inc., Deerfield, IL (US)

( * ) Notice: Subject to any disclaimer, the term of this patent is extended or adjusted under 35 U.S.C. 154(b) by 0 days.

(21) Appl. No.: 09/204,890

(22) Filed: Dec. 3, 1998

(51) Int. Cl.⁷ ............................ G01N 27/30; G01N 27/32
(52) U.S. Cl. ............................................ 204/435; 204/420
(58) Field of Search ................................................ 204/435

(56) References Cited

U.S. PATENT DOCUMENTS

| | | |
|---|---|---|
| 2,058,761 | 10/1936 | Beckman et al. . |
| 2,099,298 | 11/1937 | Fracker . |
| 2,192,123 | 2/1940 | Bennett . |
| 2,256,733 | 9/1941 | Cary et al. . |
| 2,768,135 | 10/1956 | Adelson . |
| 3,159,783 | 12/1964 | Sparnaay et al. . |
| 4,285,792 | 8/1981 | McGandy . |
| 4,415,858 | 11/1983 | Hale . |
| 4,447,309 | 5/1984 | Morioka et al. . |
| 4,582,589 | 4/1986 | Ushizawa et al. . |
| 4,609,874 | 9/1986 | Reich . |
| 5,034,113 | 7/1991 | Iwamoto . |
| 5,066,373 | 11/1991 | Levy et al. . |
| 5,116,481 | 5/1992 | Ozawa et al. . |
| 5,334,305 * | 8/1994 | Okada et al. .......................... 204/435 |
| 5,419,826 | 5/1995 | Zirino . |

FOREIGN PATENT DOCUMENTS

| | | |
|---|---|---|
| 39 34 302 A1 | 4/1990 | (DE) . |
| 195 34 925 A1 | 3/1997 | (DE) . |
| 195 42 213 A1 | 5/1997 | (DE) . |
| 0 100 988 A1 | 2/1984 | (EP) . |
| 0 484 622 A2 | 5/1992 | (EP) ............................... G01N/31/16 |
| 2 093 194 | 8/1982 | (GB) . |

* cited by examiner

Primary Examiner—T. Tung
(74) Attorney, Agent, or Firm—Mark J. Buonaiuto; Joseph A. Fuchs

(57) ABSTRACT

The present invention provides a reference electrode solution containing ammonium salts and phosphonium salts for the potentiometric measurement of pH and method of using the same. The use of the ammonium salts and the phosphonium salts to replace potassium chloride or sodium chloride as reference electrolytes in a standard reference electrode minimizes the formation of precipitates in sample solutions containing cation-sensitive compounds. Disruption of ion flow through the reference electrode is eliminated, and accurate pH measurements may be obtained in solutions that contain compounds having a strong affinity for hard cations.

30 Claims, 2 Drawing Sheets

REFERENCE ELECTRODE SOLUTION CONTAINING ORGANIC AMMONIUM AND PHOSPHONIUM SALTS FOR POTENTIOMETRIC MEASUREMENT OF PH

TECHNICAL FIELD

This invention relates to a pH electrode having a reference electrode solution containing ammonium salts and phosphonium salts for the potentiometric measurement of pH and more specifically, to the use of ammonium salts as reference electrolytes to minimize the formation of precipitates in solutions containing cation-sensitive compounds.

BACKGROUND ART

The most common uses of a pH meter are in the measurement of pH, and in chemical analyses where they are used to measure the end point of an acid-base titration. All pH meters are based on a general method of measuring the potential difference between an indicator electrode, which responds to the activity of hydrogen ion in solution, and a reference electrode whose potential remains constant throughout the course of the potentiometric measurement. This potential difference produced is proportional to the hydrogen ion activity of the sample solution, thus enabling the determination of solution pH.

The most widely used and convenient pH meter utilizes a glass membrane electrode. Membrane electrodes are those electrodes that measure the potential difference that develops across a thin glass membrane separating two solutions having different hydrogen ion concentrations. A known glass electrode 2 typically consists of an indicator electrode 4 and a reference electrode 6 immersed in a solution 8 whose pH is to be measured. (See FIG. 1.) These electrodes are connected via external leads 10 and 12 to separate terminals of a potential measuring device such as a potentiometer.

The indicator electrode 4 is typically a thin-walled glass bulb 16 containing a solution having a constant pH and a platinum wire 18 immersed in the solution. The indicator electrode solution 14 is called a buffer solution, having a known pH that does not vary with the addition of small amounts of an acid or a base.

It is also necessary to employ a reference electrode 6 to maintain an essentially constant and reproducible potential in the presence of small currents. Ideally, this electrode is entirely insensitive to the solution under study. This is distinguishable from the indicator electrode 4 whose response is dependent upon the analyte concentration.

A well-known reference electrode that is often described in the prior art may be a calomel electrode 6. An example of a standard calomel reference electrode is shown in FIG. 2. A calomel electrode utilizes a mercury chloride paste 26 contained in an inner tube 24. An outer tube 20 of the calomel electrode is typically filled with a saturated solution 22 of potassium chloride.

The potential of the calomel electrode varies directly with the chloride concentration of potassium chloride. The design of the calomel electrode may be represented as follows:

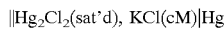

The electrode reaction of mercurous chloride is:

Another reference electrode 6 analogous to the calomel electrode is the silver/silver chloride electrode having a wire electrode 19 made of silver immersed in a solution of potassium chloride that has been saturated with silver chloride. (See FIG. 1.)
The shorthand cell representation of the silver/silver chloride electrode is:

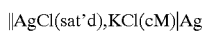

The electrode reaction of silver chloride is:

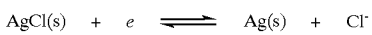

The body of both types of reference electrodes consists of an outer glass tube 20 typically filled with a solution 22 of saturated potassium chloride or other similar solution containing a hard cation component such as sodium. (See FIG. 1.) An inner tube 24 contains a saturated solution 26 of mercurous chloride or silver chloride and saturated potassium chloride. The inner tube 24 has a small opening 28 to allow for passage of ions between the two electrode compartments. The outer tube 20 is immersed in the sample solution 8, and contacts the sample solution by means of a fritted disk 30 or a porous fiber sealed in the end of the outer tubing. (See FIG. 1.) Instead of a fritted disk 30 or porous fiber, the outer tube 20 may have a ground glass sleeve 32 to achieve electrical contact with the sample solution. (See FIG. 2.)

One problem encountered with the reference electrodes in the prior art is that constituents of a sample solution 8 whose pH is to be measured, may have a strong affinity for cations. These cation-sensitive compounds may form a precipitate at the phase boundary 34 between the fritted glass channel, filled with the potassium chloride and the sample solution. (See FIG. 1.) This precipitate disrupts ion flow through this reference electrode thereby leading to electrode instability. This reaction occurs with sample solutions that interact strongly with hard cations, such as potassium or sodium, and form insoluble salts. Solutions containing hard cations such as potassium and sodium are generally used as electrolyte solutions in reference electrodes. For example, a concentrated KCl solution is used as solution 22. (See FIGS. 1 and 2.) The result of such a reaction is that the pH electrode becomes contaminated and unstable. The instability causes large errors in the pH reading, many as large as 1 pH unit, and often greater. For this reason, it is desirable to use a reference electrode solution containing an electrolyte compound, and to provide a method of using the same, such that the electrolyte comprises a non-interacting (soft) cationic compound that does not react with the sample solution to form precipitates. As will be discussed below, compounds such as quaternary ammonium salts, and quaternary phosphonium salts, when used in a reference electrode solution, serve as a replacement electrolyte without forming precipitates with constituents in the sample solution.

Ammonium salts are commonly used in the prior art for a variety of chemical applications. Noteworthy uses of these compounds include U.S. Pat. No. 5,116,481, issued to Ozawa et al. Ozawa is directed to an anion-selective sensitive film in an anion selective electrode for measuring the concentration of inorganic anions, such as chloride ions contained in body fluids. The anion-selective sensitive film contains an anion sensitive substance, such as quaternary onium salts, including quaternary ammonium salts and quaternary phosphonium salts. These anion selective substances are supported by a polymeric film containing a high polymer and plasticizer. (Column 2, lines 24–27.) Of the quaternary onium salts, phosphonium salts are preferred for their high selectivity for ceratin ions including chlorate, thiocyanate, iodide and nitrate ions and their low selectivity for other ions such as hydroxyl or fluoride ions. (Column 5, lines 17–66.) This high selectivity ability reportedly produces accurate anion measurement with longer electrode life. (Column 6, lines 10–19.) The use of ammonium salts and phosphonium salts in the present invention is readily distinguishable from their use in Ozawa. Unlike the disclosure in Ozawa, the present invention does not use quaternary ammonium salts and quaternary phosphonium salts to form an anion sensitive film or membrane. Rather, in the present invention, quaternary ammonium salts and quaternary phosphonium salts are used in a reference electrode solution in a pH electrode. Further, the reference electrode solution of the present invention is used to accurately measure the pH of a sample solution, not to measure anion concentration.

The present invention is also distinguishable from U.S. Pat. No. 5,066,373 issued to Levy et al. Levy discloses an electrode system for monitoring and controlling the pH of phenol-acetone streams used to produce phenol and to maximize and isolate useful by-products of cumene hydroperoxide, a compound used to create phenol. Levy discloses ammonium salts dissolved in a solution of phenol, acetone, and water to form an electrode solution. (Column 2, lines 35–40.)

Levy discloses the preferred use of ammonium salts in an electrolyte solution to obviate the necessity of adding an external solvent such as water, to create a time invariant voltage and to decrease contamination. (Column 2, lines 16–45.) This consistent voltage is used to continuously monitor the acidity of the neutralized cleavage mixture of phenol-acetone-cumene process streams.

The use of ammonium salts and phosphonium salts in the present invention is dissimilar to the use of ammonium salts in Levy. Unlike their use in Levy, the present invention utilizes ammonium and phosphonium salts as a replacement aqueous electrolyte to prevent the formation of precipitates with cation-sensitive constituents in sample solutions. In contrast, Levy discloses the use of ammonium salts in combination with phenol, acetone, and water to create a soluble and stable electrolyte solution. This solution is disclosed as effective in measuring the acidity of a mixture used to create phenol, not to measure the pH of solutions containing cation-sensitive compounds.

SUMMARY OF THE INVENTION

The present invention provides for the use of a reference electrode solution containing ammonium salts or phosphonium salts for the potentiometric measurement of pH. The use of ammonium and phosphonium salts in reference electrolyte solutions minimizes the formation of precipitates in sample solutions containing cation-sensitive compounds. The term "cation-sensitive" means any solution comprising constituents (simple solutes, colloidal solutes, dispersed solids) that can react with cations in the reference solution of a pH electrode and disrupt the ion flow through the electrode. Hard cations include all Group IA elements such as potassium, all Group IIA elements, all transition elements in Groups I through VIIIB, the lanthanide and actinide series, and additional elements in Groups IIIA through VIA which include aluminum, gallium, germanium, indium, tin, antimony, thallium, lead, bismuth and polonium. A cation-sensitive compound, when reacted with any or a combination of the aforementioned metal ions causes contamination of the reference electrode such that stable pH readings are not possible. This contamination includes, but is not limited to, precipitate formation at the ion junction whether in the embodiment of a fritted disk or channel (30 in FIGS. 1 and 3) or a sleeve (32 in FIG. 2). Further, the replacement of potassium chloride solutions with a solution containing ammonium salts or phosphonium salts results in pH readings that are stable and accurate over a wide electrolyte concentration range.

According to the present invention, a reference electrode for measuring the pH of a cation-sensitive compound is provided. The known reference electrolyte compound of potassium chloride or other similar cation compound is replaced, in the reference electrode solution, with a compound having the general structure:

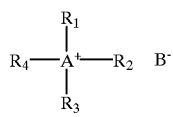

wherein $R_1$, $R_2$, $R_3$, and $R_4$ are hydrogen or organic substituents such as alkyl, alkenyl, and aryl. A is a nitrogen or phosphorous atom. B is a counterion such as a halogen ion of fluoride, chloride, bromide, or iodide. B may also be an oxyanion such as nitrate, sulfate, phosphate, carbonate, bromate, chlorate, or iodate. Counterion B may also be an organic anion such as a sulfonate (e.g. methylsulfonate), carboxylate (e.g. acetate, or benzoate), or cyanide ($CN^-$).

Several organic substituents may be used as $R_1$, $R_2$, $R_3$, and $R_4$. Alkyl substituents are straight or branched hydrocarbon chains such as methyl, ethyl, n-propyl, isopropyl, n-butyl, isobutyl, sec-butyl and tert-butyl, pentyl, neopentyl, hexyl, isohexyl, and the like. These substituents have the general formula $C_nH_{2n+1}$ wherein n is a positive integer. Preferably, alkyl substituents such as methyl and ethyl are used. The methyl substituent is an example of a preferred alkyl substituent used in the present invention. Four methyl substituents bonded to nitrogen form the positively charged tetramethylammonium ion. This cation may combine with a halogen counterion to produce a preferred compound referred to as an quaternary ammonium salt.

The reference electrolyte compound of the present invention may also use alkenyl substituents. Alkenyl substituents are unsaturated acyclic hydrocarbon chains containing at least one double bond. They have the general formula $C_nH_{2n+1-s}$ wherein n is a positive integer and s is equal to the number of unsaturations in the molecule. Preferred alkenyl substituents are ethenyl, propenyl, butenyl, isobutenyl, pentenyl, hexenyl, or other known alkenyl substituents. Alkenyl substituents ethenyl and propenyl are more commonly known as vinyl and allyl.

Also, the reference electrolyte compound may include aryl substituents which are organic substituents derived from an aromatic hydrocarbon by the removal of one atom. A common aryl substituent is phenyl, having the general formula $C_6H_5$. Other aryl substituents may include naphthyl and biphenyl. Alkyl substituents with attached aryl substituents are also included such as benzyl, 1-phenylethyl, 2-phenylethyl, 1-phenylpropyl, 2-phenylpropyl, 3-phenylpropyl, and the like.

Another organic substituent may be hetrosubstituted hydrocarbon chains having formula $C_nH_mX_xY_yZ_z$, wherein n,m,x,y, and z are positive integers. Heterosubstituted substituents include heteroalkyl and heteroaryl substituents including pyridinyl, pyrazinyl, pyrimidinyl, pyrrolyl, thienyl, thiazolyl, furyl, pyrazolyl, imidazolyl, triazolyl, tetrazolyl, and quinolinyl, among many others. X,Y, and Z refer to heteroatoms such as nitrogen, sulfur or oxygen.

When the present invention utilizes a mercurous chloride electrode for measuring the pH of a cation-sensitive compound, the shorthand cell representation is as follows:

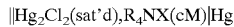

wherein R is an organic substituent and X is a counterion such as a halogen or oxyanion, and c is the molar concentration of $R_4NX$.

When the present invention is a silver/silver chloride electrode for measuring the pH of a cation-sensitive compound, the electrode may be represented as follows:

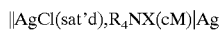

wherein R is an organic substituent and X is a counterion such as halogen or oxyanion, and c is the molar concentration.

The present invention also provides for a method of using a reference electrode in the measurement of pH of solutions containing cation-sensitive solutes. The method consists of providing a reference electrode having an electrical lead and an outer and inner tube, providing a reference electrolyte compound in the inner and outer tube, the compound having the formula $R_4AB$, wherein R is hydrogen, or an organic substituent such as alkyl, alkenyl, or aryl, and A is a nitrogen or phosphorous atom and B is a counterion such as a halogen or an oxyanion, immersing the outer tube of the reference electrode in a sample solution, and maintaining a constant and reproducible potential in the presence of small currents.

The reference electrode may be separate from the indicator electrode (FIGS. 1 and 2), or part of a combination electrode (FIG. 3) in which the reference cell and indicator cell are incorporated into one electrode. FIG. 3 shows a typical combination glass electrode for measuring pH. The reference electrolyte solution is introduced into the electrode through the fill port (35).

DETAILED DESCRIPTION

Figure 1:
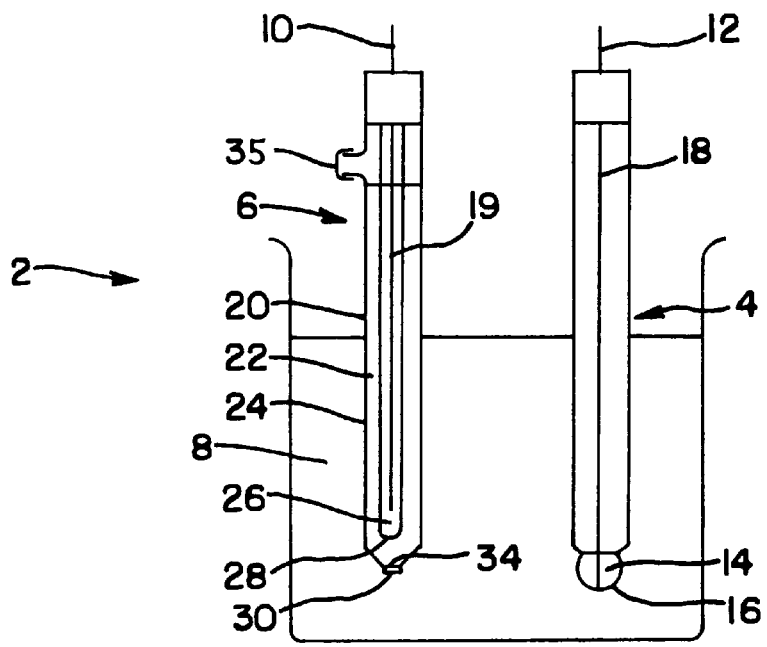
FIG. 1 is a perspective view of an indicator electrode and a reference electrode.

While the invention is susceptible of embodiment in many different forms, there is shown in the drawings and will herein be described in detail preferred embodiments of the invention with the understanding that the present disclosure is to be considered as an exemplification of the principles of the invention and is not intended to limit the broad aspect of the invention to the embodiments illustrated.

FIG. 1 of the present invention shows a standard glass electrode 2 containing an indicator electrode 4 and a reference electrode 6 immersed in a solution 8 whose pH is to be measured. The electrodes are connected via external leads 10 and 12 to separate terminals of a potential measuring device.

Figure 2:
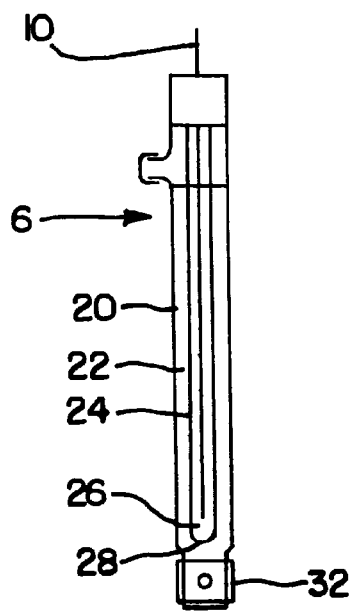
FIG. 2 is a perspective view of an alternative reference electrode having a glass sleeve.
Figure 3:
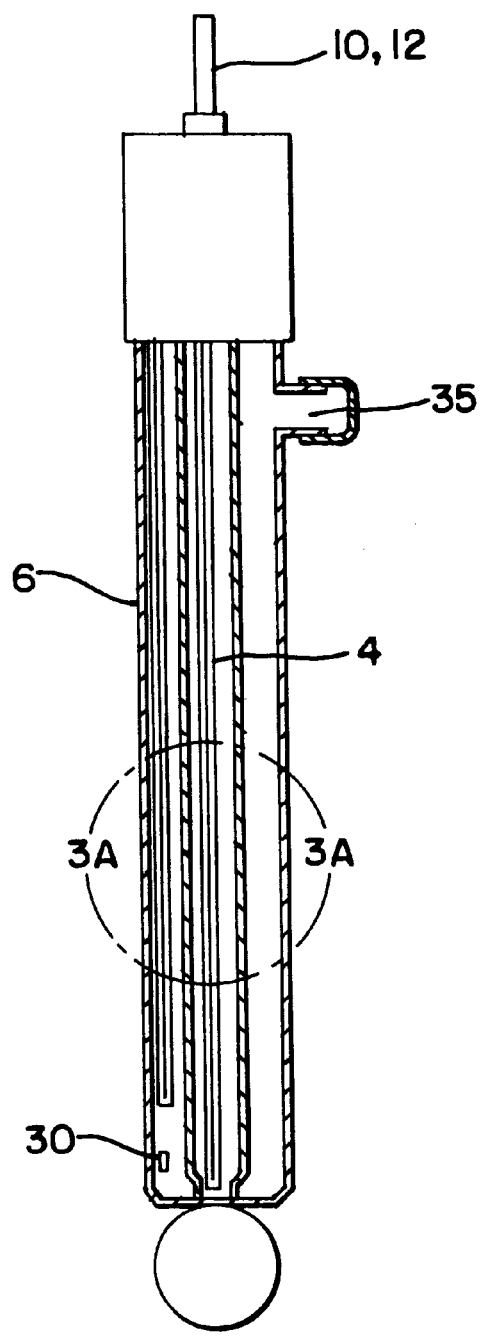
FIG. 3 is a perspective view of a combination glass electrode.
Figure 3A:
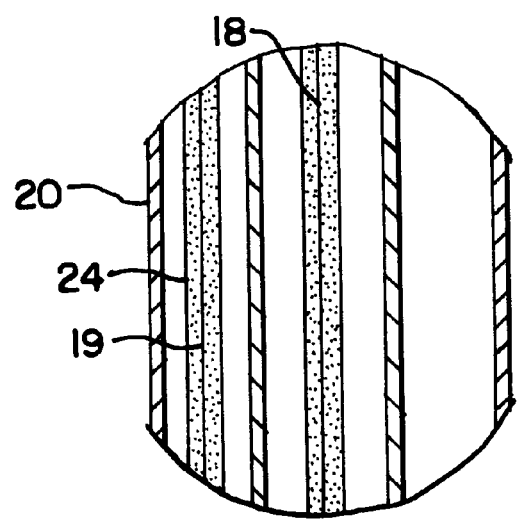
FIG. 3A is an expanded view of a portion of the electrode shown in FIG. 3.

The reference electrode 6 has an outer glass tube 20 and an inner tube 24 which contains a solution or suspension 26 of mercurous chloride or silver chloride and saturated potassium chloride. A fluid path between the inner solution 26 and solution 22 in the outer tube 18 is provided by a small opening 28. The outer tube 20 is immersed into the sample solution 8, which contacts the solution 22 by means of a fritted disk 30 or a porous fiber seated in the end of the outer tubing. Instead of a fritted disk 30 or porous fiber, FIG. 2 illustrates that the outer tube 18 may have a ground glass sleeve 32 to achieve electrical contact with the sample solution 8. (See FIG. 2.)

The outer glass tube 20 is typically filled with a solution 22 of a reference electrolyte compound, which serves as a non-interacting (soft) cation compound, having the general structure:

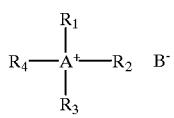

wherein $R_1$, $R_2$, $R_3$, and $R_4$ are hydrogen, alkyl, alkenyl, or aryl substituents and A is a nitrogen or phosphorous atom and B is a counterion selected from the group of either a halogen ion, cyanide, or oxyanion.

The preferred reference electrolyte compound comprises quaternary ammonium salts or quaternary phosphonium salts of alkyl and aryl radicals such as tetramethylammonium fluoride, tetramethylammonium chloride, tetramethylammonium bromide, tetramethylammonium iodide, tetraethylammonium fluoride, tetraethylammonium chloride, tetraethylammonium bromide, tetraethylammonium iodide, tetra-n-propylammonium fluoride, tetra-n-propylammonium chloride, tetra-n-propylammonium bromide, tetra-n-propylammonium iodide, tetra-n-butylammonium fluoride, tetra-n-butylammonium chloride, tetra-n-butylammonium bromide, tetrapentylammonium fluoride, tetrapentylammonium chloride, tetrapentylammonium bromide, tetrapentylammonium iodide, tetrahexylammonium fluoride, tetrahexylammonium chloride, tetrahexylammonium bromide, tetrahexylammonium iodide, tetraheptylammonium fluoride, tetraheptylammonium chloride, tetraheptylammonium bromide, tetraheptylammonium iodide, tetraoctylammonium fluoride, tetraoctylammonium chloride, tetraoctylammonium bromide, tetraoctylammonium iodide, tetranonylammonium fluoride, tetranonylammonium chloride, tetranonylammonium bromide, tetranonylammonium iodide, tetradecylammonium fluoride, tetradecylammonium chloride, tetradecylammonium bromide, tetradecylammonium iodide, tetrahexadecylammonium fluoride, tetrahexadecylammonium chloride, tetrahexadecylammonium bromide, tetrahexadecylammonium iodide, tetraoctadecylammonium fluoride, tetraoctadecylammonium chloride, tetraoctadecylammonium bromide, tetraoctadecylammonium iodide, tetradecyltrimethylammonium fluoride, tetradecyltrimethylammonium chloride, tetradecyltrimethylammonium bromide, tetradecyltrimethylammonium iodide, tetrabenzylammonium fluoride, tetrabenzylammonium chloride, tetrabenzylammonium bromide, tetrabenzylammonium iodide, or tetra-n-butylammonium iodide, tetraphenylammonium fluoride, tetraphenylammonium chloride, tetraphenylammonium bromide, tetraphenylammonium iodide, and an appropriate solvent.

While specific embodiments have been illustrated and described, numerous modifications are possible without departing from the spirit of the invention, and the scope of protection is only limited by the scope of the accompanying claims.

EXAMPLE

The pH measurement for a solution containing 6,7-dichloro-5-nitro-1,4-dihydroquinoxaline-2,4-dione was obtained by use of a conventional glass pH electrode (silver/silver chloride combination pH glass electrode was used (Ross® Sure-Flow™, Model No. 8172). This compound, depicted below, was found to have a strong affinity for cations.

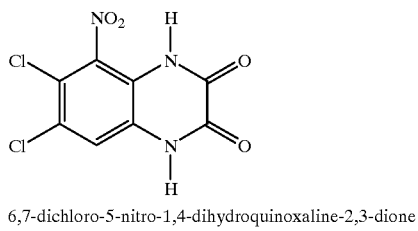

6,7-dichloro-5-nitro-1,4-dihydroquinoxaline-2,3-dione

The outer tube of the reference electrode was filled with a 3 M solution of potassium chloride. When immersed in the sample solution of 6,7-dichloro-5-nitro-1,4-dihydroquinoxaline-2,3-dione, the potassium chloride reacted with the sample solution to form a potassium salt of 6,7-dichloro-5-nitro-1,4-dihydroquinoxaline-2,3-dione and this reaction formed a precipitate at the phase boundary (reference junction) between the fritted glass channel and the sample solution.

pH measurement of the solution was unstable, and the reading drifted during a single measurement. The pH of the solution measured subsequent to the assay of the sample solution resulted in large errors as much as 1 pH unit or greater evidencing electrode contamination.

When the potassium chloride solution was replaced with a 3 M solution of tetramethylammonium chloride, the pH readings taken were accurate and stable within one minute after immersion of the electrode in the sample solution. Readings remained stable for several hours after immersion, and the pH measurements were in close agreement of within 0.1 unit. The experiment was repeated over an electrolyte concentration range of 2 M to 5.5 M and found to yield identical results.

The experiment was also repeated using a variety of standard glass electrodes from various suppliers. Solution pH was successfully measured in each case and the results were closely similar to that described above.

What is claimed is:

1. A reference electrode used to measure the pH of an aqueous medium containing a cation-sensitive compound, the electrode comprising an electrode solution consisting of:

an electrolyte compound having the structure:

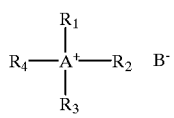

wherein $R_1$, $R_2$, $R_3$, and $R_4$ are selected from the group consisting of alkyl, alkenyl, and aryl substituents and wherein A is an atom selected from the group consisting of nitrogen and phosphorous and wherein B is a cyanide ion and an appropriate solvent.

2. The reference electrolyte compound of claim 1, wherein $R_1$, $R_2$, $R_3$, and $R_4$ are alkyl substituents having the formula $C_nH_{2n+1}$ wherein n is a positive integer.

3. The reference electrolyte compound of claim 2, wherein $R_1$, $R_2$, $R_3$, and $R_4$ are alkyl substituents selected from the group consisting of methyl, ethyl, n-propyl, isopropyl, n-butyl, isobutyl, sec-butyl, tert-butyl, n-pentyl, 1-methylbutyl, 2-methylbutyl, 3-methylbutyl, 1,1-dimethylpropyl, 1,2-dimethylpropyl, neopentyl, hexyl, isohexyl, heptyl, octyl, nonyl, decyl, tetradecyltrimethyl, hexadecyl, and octadecyl.

4. The reference electrolyte compound of claim 1, wherein $R_1$, $R_2$, $R_3$, and $R_4$ are alkenyl substituents having the formula $C_nH_{2n+1-s}$ wherein n is a positive integer and s is equal to the number of unsaturations in the molecule.

5. The reference electrolyte compound of claim 1, wherein $R_1$, $R_2$, $R_3$, and $R_4$ are alkenyl substituents selected from the group consisting of ethenyl, propenyl, butenyl, isobutenyl, pentenyl, and hexenyl.

6. The reference electrolyte compound of claim 1, wherein $R_1$, $R_2$, $R_3$, and $R_4$ are aryl substituents selected from the group consisting of phenyl, naphthyl, and biphenyl.

7. The aryl substituent of claim 6, wherein the aryl substituent is phenyl having the general formula $C_6H_5$—.

8. The reference electrolyte compound of claim 1 wherein A is a nitrogen atom.

9. The reference electrolyte compound of claim 1 wherein A is a phosphorous atom.

10. A reference electrode used to measure the pH of an aqueous medium containing a cation-sensitive compound, the electrode comprising an electrode solution consisting of:

an electrolyte compound having the structure

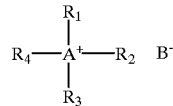

wherein $R_1$, $R_2$, $R_3$, and $R_4$ are aryl-substituted alkyl substituents selected from the group consisting of benzyl, 1-phenylethyl, 2-phenylethyl, 1-phenylpropyl, 2-phenylpropyl, and 3-phenylpropyl and wherein A is an atom selected from the group consisting of nitrogen and phosphorous and wherein B is a counterion selected from the group consisting of halogen, oxyanion, and a cyanide anion; and an appropriate solvent.

11. The reference electrolyte compound of claim 10, wherein counterion B– is a halogen ion selected from the group consisting of fluoride, chloride, bromide, and iodide.

12. The reference electrolyte compound of claim 11, wherein counter ion B– is a chloride ion.

13. The reference electrolyte compound of claim 10, wherein counterion B– is an oxyanion selected from the group consisting of nitrate, sulfate, hydrogen sulfate, carboxylate, carbonate, bicarbonate, bromate, iodate, chlorate, phosphate, hydrogen phosphate, methylsulfonate, p-tolylsulfonate, and trifluoromethylsulfonate.

14. A reference electrode for measuring the pH of a cation-sensitive compound, the electrode containing a solution comprising a reference electrolyte compound having the structure:

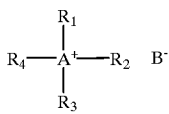

wherein $R_1$, $R_2$, $R_3$, and $R_4$ are hetero substituted substituents having formula $C_nH_mX_xY_yZ_z$ wherein n, m, x, y, and z are positive integers and X, Y and Z are selected from the group consisting of nitrogen, sulfur, and oxygen, and wherein A is selected from the group consisting of a nitrogen atom and a phosphorous atom and wherein B is a counterion selected from the group consisting of halogens, oxyanions, and cyanide ion, and an appropriate solvent.

15. The reference electrolyte compound of claim 14, wherein B– is a halogen ion selected from the group consisting of fluoride, chloride, bromide, and iodide.

16. The reference electrolyte compound of claim 14, wherein B– is an oxyanion selected from the group consisting of nitrate, sulfate, hydrogen sulfate, carboxylate, carbonate, bicarbonate, bromate, iodate, chlorate, phosphate, hydrogen phosphate, methylsulfonate, p-tolylsulfonate, and trifluoromethylsulfonate.

17. The reference electrolyte compound of claim 14 wherein $B^-$ is cyanide ion.

18. The reference electrolyte compound of claim 14, wherein the hetero substituted substituents are selected from the group consisting of pyridinyl, pyrazinyl, pyrimidinyl, pyrrolyl, thienyl, thiazolyl, furyl, pyrazolyl, imidazolyl, triazolyl, tetrazolyl, and quinolinyl.

19. A reference electrode used to measure the pH of an aqueous medium containing a cation-sensitive compound, the electrode comprising an electrode solution consisting of:
an electrolyte compound having the structure:

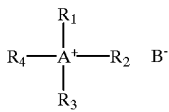

wherein $R_1$, $R_2$, $R_3$, and $R_4$ are selected from the group consisting of alkyl, alkenyl, and aryl substituents and wherein A is a phosphorous atom and wherein B is a counterion selected from the group consisting of halogen, oxyanion, and a cyanide ion anion; and
an appropriate solvent.

20. The reference electrolyte compound of claim 19, wherein $R_1$, $R_2$, $R_3$, and $R_4$ are alkyl substituents having the formula $C_nH_{2n+1}$ wherein n is a positive integer.

21. The reference electrolyte compound of claim 20, wherein $R_1$, $R_2$, $R_3$, and $R_4$ are alkyl substituents selected from the group consisting of methyl, ethyl, n-propyl, isopropyl, n-butyl, isobutyl, sec-butyl, tert-butyl, n-pentyl, 1-methylbutyl, 2-methylbutyl, 3-methylbutyl, 1,1-dimethylpropyl, 1,2-dimethylpropyl, neopentyl, hexyl, isohexyl, heptyl, octyl, nonyl, decyl, tetradecyltrimethyl, hexadecyl, and octadecyl.

22. The reference electrolyte compound of claim 19, wherein $R_1$, $R_2$, $R_3$, and $R_4$ are alkenyl substituents having the formula $C_nH_{2n+1-s}$ wherein n is a positive integer and s is equal to the number of unsaturations in the molecule.

23. The reference electrolyte compound of claim 19, wherein $R_1$, $R_2$, $R_3$, and $R_4$ are alkenyl substituents selected from the group consisting of ethenyl, propenyl, butenyl, isobutenyl, pentenyl, and hexenyl.

24. The reference electrolyte compound of claim 19, wherein $R_1$, $R_2$, $R_3$, and $R_4$ are aryl substituents selected from the group consisting of phenyl, naphthyl, and biphenyl.

25. The aryl substituent of claim 24, wherein the aryl substituent is phenyl having the general formula $C_6H_5-$.

26. The reference electrolyte compound of claim 19, wherein $R_1$, $R_2$, $R_3$, and $R_4$ are aryl-substituted alkyl substituents selected from the group consisting of benzyl, 1-phenylethyl, 2-phenylethyl, 1-phenylpropyl, 2-phenylpropyl, and 3-phenylpropyl.

27. The reference electrolyte compound of claim 19, wherein counterion B– is a halogen ion selected from the group consisting of fluoride, chloride, bromide, and iodide.

28. The reference electrolyte compound of claim 27, wherein counterion $B^-$ is a chloride ion.

29. The reference electrolyte compound of claim 19, wherein counterion B– is an oxyanion selected from the group consisting of nitrate, sulfate, hydrogen sulfate, carboxylate, carbonate, bicarbonate, bromate, iodate, chlorate, phosphate, hydrogen phosphate, methylsulfonate, p-tolylsulfonate, and trifluoromethylsulfonate.

30. The reference electrolyte compound of claim 19, wherein counterion $B^-$ is cyanide ion.

* * * * *

UNITED STATES PATENT AND TRADEMARK OFFICE
CERTIFICATE OF CORRECTION

PATENT NO.   : 6,221,222 B1                                              Page 1 of 1
DATED        : April 24, 2001
INVENTOR(S)  : James Kipp et al.

It is certified that error appears in the above-identified patent and that said Letters Patent is hereby corrected as shown below:

Column 8,
Line 6, change "$C_nH_{2+1}$" to -- $C_nH_{2n+1}$ --
Line 17, change "$C_nH_{2+1-s}$" to -- $C_nH_{2n+1-s}$ --

Signed and Sealed this

Eighth Day of January, 2002

Attest:

Attesting Officer

JAMES E. ROGAN
*Director of the United States Patent and Trademark Office*